United States Patent [19]
Cohen et al.

[11] Patent Number: 5,993,803
[45] Date of Patent: Nov. 30, 1999

[54] METHOD OF REDUCING THE SEVERITY OF HOST VS GRAFT REACTION BY DOWN-REGULATING HSP60 AUTOIMMUNITY

[75] Inventors: Irun R. Cohen, Rehovot, Israel; Ohad Birk, Rockville, Md.

[73] Assignee: Yeda Research and Development Co., Ltd., Rehovot, Israel

[21] Appl. No.: 08/706,209

[22] Filed: Aug. 30, 1996

[51] Int. Cl.$^6$ .......................... A61K 39/00; A61K 38/00; A01N 63/00
[52] U.S. Cl. ..................... 424/93.71; 424/185.1; 424/283.1; 514/12; 514/21
[58] Field of Search .................... 514/12, 21; 424/185.1, 424/283.1, 93.71

[56] References Cited

U.S. PATENT DOCUMENTS 5,356,779  10/1994  Mozes et al. .

FOREIGN PATENT DOCUMENTS

WO92/04049  3/1992  WIPO .
WO97/01959  1/1997  WIPO .
WO97/02016  1/1997  WIPO .

OTHER PUBLICATIONS

Elias et al Diabetes vol. 44 Sep. 1995 pg. 1132–1138.
Alevy et al Transplantation Mar. 27, 1996 vol. 61, No.:6 pg. 963–967.

*Primary Examiner*—Anthony C. Caputa
*Assistant Examiner*—Geetha P. Bansal
*Attorney, Agent, or Firm*—Browdy and Neimark

[57] ABSTRACT

A method for reducing the severity of host vs graft reaction (HVGR) by the transplant recipient of donor organ or tissue by the transplant recipient and is based on the discovery that hsp60 autoimmunity can function as an accelerator of foreign immunity and the down-regulation of hsp60 autoimmunity suppresses or prevents the graft rejection reaction. Administration of any composition which causes the down-regulation of hsp60 autoimmunity, such as hsp60 or peptide p277 in a tolerogenic carrier or a biologically active carrier capable of mediating a TH1→TH2 shift, will thus reduce the severity of HVGR.

11 Claims, 4 Drawing Sheets

METHOD OF REDUCING THE SEVERITY OF HOST VS GRAFT REACTION BY DOWN-REGULATING HSP60 AUTOIMMUNITY

BACKGROUND OF THE INVENTION

1. Field of the Invention

The present invention relates to a method of reducing the severity of host vs graft reaction (HVGR) by down-regulating autoimmunity to heat shock protein hsp60. In particular, the present invention relates to the use of hsp60 protein or hsp60 epitope peptides to suppress graft rejection by down-regulating hsp60 autoimmunity.

2. Description of the Background Art

Autoimmune disorders, e.g., insulin-dependent diabetes mellitus (IDDM or type I diabetes), multiple sclerosis, rheumatoid arthritis and thyroiditis, are characterized by reactivity of the immune system to an endogenous antigen, with consequent injury to tissues. These immune responses to self-antigens are maintained by the persistent activation of self-reactive T lymphocytes.

The 60 kDa heat shock protein (hsp60) is a stress protein expressible in all of the cells of the body. Nevertheless, healthy individuals manifest a high frequency of autoimmune T cells specific for hsp60 self-epitopes. Normal healthy mice and human beings have been shown to have T cells targeted at their self hsp60 antigen (Kaufmann, 1990; Kaufmann et al., 1994; Young, 1989; Cohen, 1992b). However, these autoimmune T cells are also involved in T cell mediated autoimmune diseases: a high concentration of T cells targeted at self hsp60 antigen have been found in the autoimmune lesions of human chronic arthritis (Cohen, 1991; Res et al., 1989; van Eden et al., 1989), multiple sclerosis (Selmaj et al., 1991), experimental autoimmune encephalomyelitis (Selmaj et al., 1991) and adjuvant arthritis (Hogervorst et al., 1992). Anti-hsp60 T-cells have also been shown to play a role in diabetes mellitus in the non-obese diabetic (NOD) mouse model (Elias et al., 1990; Elias et al., 1991; Elias et al., 1994; Elias et al., 1995; Birk et al., 1996a; Birk et al., 1993; Cohen , 1991).

NOD mice spontaneously develop type I diabetes caused by autoimmune T cells that attack the insulin-producing β cells of the islets. The autoimmune attack is associated with T-cell reactivity to a variety of self-antigens including a peptide of the 60 kDa heat shock protein (hsp60) and peptides of glutamic acid decarboxylase (GAD). Thus, for example, spontaneous diabetes developing in the NOD/Lt strain of mice could b e treated with hsp60 (U.S. Pat. No. 5,114,844) or with antigenic fragments thereof, such as the peptide designated p277 corresponding to positions 437–460 of the human hsp60 sequence (PCT Patent Publication No. WO90/10449); variants of the p277 peptide in which one or both cysteine residues at positions 6 and/or 11 have been replaced by valine and/or the Thr residue at position 16 is replaced by Lys (see PCT Publication WO96/19236); or various other peptides such as those designated p12 and p32, corresponding to positions 166–185 and 466–485, respectively, of the human hsp60 sequence (see PCT application PCT/US96/11375). Note that the hsp60 protein was formerly designated hsp65 but is now designated hsp60 in view of more accurate molecular weight information; by either designation the proteins are the same.

Immunization to hsp60 or peptide p277 in an appropriate adjuvant is known to induce IDDM (WO90/10449) when the immunization triggers a TH1 response. However, vaccination with hsp60 or peptide p277 without an effective adjuvant, and preferably with a tolerogenic carrier or, more preferably, with a TH2-inducing active carrier, can produce a resistance to the autoimmune process of IDDM. Subcutaneous administration of p277 in incomplete Freund adjuvant (IFA; mineral oil) led to the arrest of disease progression in young NOD mice (Elias et al., 1991) or in 12–17 week old NOD mice with advanced insulitis (Elias et al., 1994 and 1995). Both the human (Elias et al., 1994 and 1995) and mouse (Birk et al., 1996a) variants of p277 were effective. NOD mice transgenic for the mouse hsp60 gene on an MHC class II promoter showed down-regulation of their spontaneous T-cell proliferative response to p277 and a significant proportion of the mice were spared the development of diabetes (Birk et al., 1996b). Moreover, administration of p277 to C57BL/KsJ mice aborted the development of autoimmune diabetes in mice that had earlier received a very low dose of the β-cell toxin streptozotocin (STZ); treatment of these mice with a peptide of the GAD65 molecule was not effective (Elias et al., 1996). Preferred TH2-inducing active carriers for use in the administration of such hsp60 fragments are certain fat emulsions, such as Intralipid or Lipofundin (see PCT/US96/11373).

Furthermore, T cells reactive to hsp60 and other hsp molecules have been isolated from cardiac allografts (Moliterno et al., 1995) as well as from other inflammatory lesions (Selmaj et al., 1991; Mor et al., 1992). Thus, anti-hsp60 autoimmune T cells accumulate at sites of inflammation. Donor-specific alloreactive T lymphocytes exhibiting such characteristics as cytolytic activity and lymphokine production are believed to mediate transplant rejection where hsp-reactive T cells may play a role in the immune cascade of the inflammatory process in transplant rejection (Moliterno et al., 1995).

It has recently been discovered by the laboratory of the present inventors that the successful treatment of the autoimmune process in IDDM by administration of the peptide p277 in oil is caused by the effect of this treatment in aborting TH1-type autoimmunity to several different antigens and instead activating p277 autoimmunity into a TH2 mode. T cells of the CD4 "helper" type have been divided into two groups, TH1 and TH2, by the characteristic cytokines they secrete when activated (Mosmann et al, 1989). TH1 cells secrete IL-2, which induces T cell proliferation, and cytokines such as IFN-γ, which mediate tissue inflammation. TH2 cells, in contrast, secrete IL-4 and IL-10. IL-4 helps cells secrete antibodies of certain IgG isotypes and suppresses the production of TH1 inflammatory cytokines (Abas et al., 1994). IL-10 indirectly inhibits TH1 activation by affecting antigen-presentation and inflammatory cytokine production by macrophages (Moore et al., 1993). It is the TH1 cells which contribute to the pathogenesis of organ-specific autoimmune diseases. TH1-type responses also appear to be involved in other T cell mediated diseases or conditions, such as contact dermatitis (Romagnani, 1994). Thus, a disease with a spectrum of autoreactivities can be turned off with a single peptide capable of inducing a T cell cytokine shift.

Transplantation is presently the treatment of choice for organ failure. During the 1980s, the discovery of cyclosporin A played a role in the significant increase in graft survival. But the use of transplants is still limited because of the acute immune rejection phenomenon (host vs graft rejection, or HVGR) which may destroy the transplanted tissue within days to months after the surgery. Control and regulation of HVGR are crucial to the development of better transplantation methods.

Nonspecific immunosuppressive therapy in an adult patient is usually through cyclosporin, started intravenously at the time of transplantation, and given orally once feeding is tolerated. Typically, methylprednisone is started also at the time of transplantation, then reduced to a maintenance dose. Azathioprine is also often used in conjunction with prednisone to achieve adequate immunosuppression. Whereas the objective of immunosuppression is to protect the transplant, general or excessive immunosuppression may lead to undesirable complications, e.g., opportunistic infections and potential malignancies. The toxicity of the immunosuppressive drugs is dose-dependent.

Means to diminish or eliminate HVGR have been long sought in the art. Any process capable of reducing the vigor of the rejection process and reducing the doses of immunosuppressive drugs needed to maintain the graft would be a significant advance in this art.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to provide a method of suppressing or preventing graft rejection of donor organ or tissue in a transplant recipient.

The present invention relates to the discovery that when the heat shock protein hsp60, or peptides and analogs thereof, are administered in a recipient subject before transplantation of organ or tissue, autoimmunity to hsp60 is down-regulated, resulting in the prevention or suppression of graft rejection of the transplanted organ or tissue.

In experiments on whether hsp60 autoimmunity, observed in autoimmune disease, was involved in transplant rejection, the laboratory of the present inventors demonstrated that expression of hsp60 is up-regulated in donor skin during rejection. The rejection of foreign skin grafts in mice was further investigated and it was observed that transgenic skin grafts hyper-expressing self-hsp60 underwent accelerated rejection by normal mice when the grafts also bore either major or minor foreign histocompatibility antigens. However, when recipient mice constitutively hyper-express self-hsp60, they not only showed depressed hsp60 autoimmunity but also showed delayed rejection of foreign skin grafts. Transplant recipients can be made to tolerate foreign grafts when their hsp60 autoimmunity is reduced by prior administration of hsp60 or hsp60 peptides and peptide analogs. Thus, the present inventors have made the surprising discovery that autoimmunity can regulate foreign immunity. When hsp60 autoimmunity is enhanced, foreign immunity and graft rejection is also enhanced; when hsp60 autoimmunity is reduced or down-regulated, foreign immunity and graft rejection is suppressed or prevented.

Thus, the present invention involves a method of suppressing or preventing graft rejection by treating a transplant recipient subject so as to cause a down-regulation of hsp60 autoimmunity in the transplant recipient either prior to the transplantation of organ or tissue, simultaneous therewith or shortly thereafter, preferably immediately prior thereto.

The hsp60 autoimmunity can be down-regulated in any known manner and preferably by the means already known for the down-regulation of hsp60 autoimmunity in the treatment of IDDM. Thus, the down-regulation can be accomplished by administering a pharmaceutical composition which includes a compound capable of down-regulating hsp60 autoimmunity such as hsp60 or a peptide fragment of hsp60 or an analog salt or functional derivative thereof. Examples of such compounds are human hsp60 (SEQ ID NO:1) and the following amino acid residues from SEQ ID NO:1: residues 31–50, residues 136–155, residues 151–170, residues 166–185, residues 195–214, residues 255–274, residues 286–305, residues 346–365; residues 421–440, residues 436–455, residues 437–460, residues 466–485, residues 511–530, residues 343–366, and residues 458–474. Examples of analogs which may be used include the peptides of SEQ ID NO:2, SEQ ID NO:3, SEQ ID NO:4, SEQ ID NO:5, SEQ ID NO:6, SEQ ID NO:7 and SEQ ID NO:8. The compound is preferably administered in a tolerogenic carrier such as incomplete Freund's adjuvant or in a biologically active carrier which helps to induce a TH1TH→2 shift, such as a fat emulsion comprising 10%–20% triglycerides of plant and/or animal origin; 1.2% –2.4% phospholipids of plant and/or animal origin; 2.25%–4.5% osmoregulator; 0%–0.05% antioxidant; and sterile water.

The present invention further relates to a means for selecting an optimum hsp60 peptide or analog for down-regulating hsp60 autoimmunity in the specific individual to be treated. Antigen-presenting cells of peripheral blood lymphocytes isolated from the blood of the individual may be contacted with a panel of individual peptides. The peptide having the optimum effect on hsp60 immunity as a result of this screen would be selected as the optimum antigen for the vaccine to be used with this particular individual to prevent graft rejection.

Hsp60, hsp60 peptides, and analogs, salts and functional derivatives thereof may be used for the preparation of a pharmaceutical composition for down-regulating hsp60 autoimmunity in a host and for down-regulating the severity of host vs graft reaction in organ transplantation.

BRIEF DESCRIPTION OF THE DRAWINGS

FIG. 2A shows that Eα-hsp60 transgenic skin is not rejected when transplanted to wild type NOD mice and FIG. 2B shows that Eα-hsp60 transgenic mice do not reject wild type skin. FIG. 2C shows the accelerated rejection ($p<0.0001$) of Eα-hsp60 transgenic NOD skin (diamonds) compared to wild type NOD skin transplanted to BALB/c mice (squares). FIG. 2D shows the accelerated rejection ($p<0.038$) of Eα-hsp60 transgenic male NOD skin transplanted to HY incompatible, wild-type female NOD mice. FIG. 2E shows the delay in rejection ($p=0.004$) of allogenic C57BL/6 (H-$2^b$) skin by Eα-hsp60 transgenic NOD mice (H-$2^{g7}$). FIG. 2F shows the delay in rejection ($p=0.001$) of BALB/k CH-2k skin by Eα-hsp60 transgenic mice. Each group contained 10–12 mice.

FIGS. 3A and 3B show the effects of treating C57BL6 (H-$2^b$) mice (FIG. 3A)

Figure 3A:
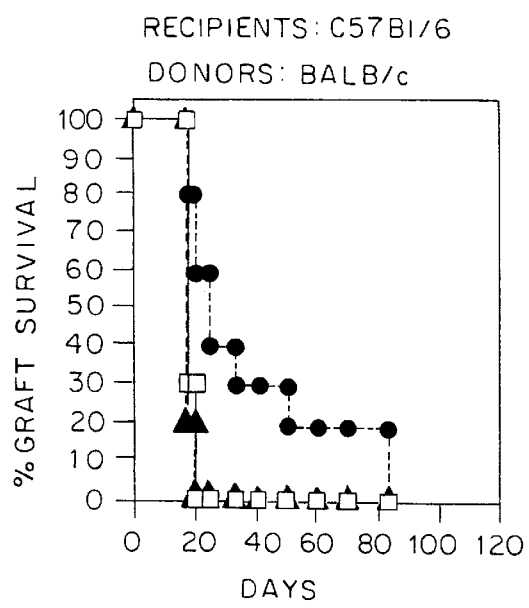
FIGS. 3A–B show that treatment with hsp60 or hsp60 peptides induces delayed rejection of skin allografts as measured by graft survival over time.
Figure 3B:
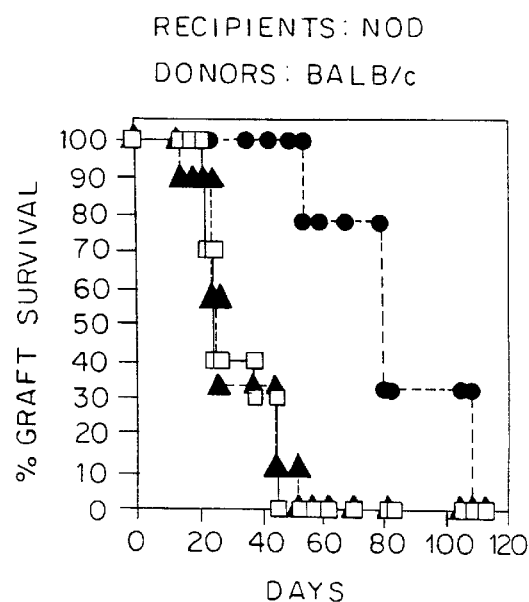

or wild-type NOD (H-2$^{g7}$) mice (FIG. 3B) with hsp60 (50 μg in incomplete Freund's adjuvant; Sigma) administered subcutaneously in the back 2 weeks before transplantation of BALB/c (H-2$^d$) skin (Elias et al., 1994; Elias et al., 1995). Recombinant human hsp60 was prepared as described (Elias et al., 1990). Control mice were untreated (open squares) or treated with incomplete Freund's adjuvant containing 50 μg of recombinant glutathione transferase (open diamonds). The differences in rejection between treatment with hsp60 (closed squares), and the controls, as determined using the Wilcoxon test, were significant ($p<0.05$ for FIG. 3A and $p<0.0001$ for FIG. 3B).

Figure 4:
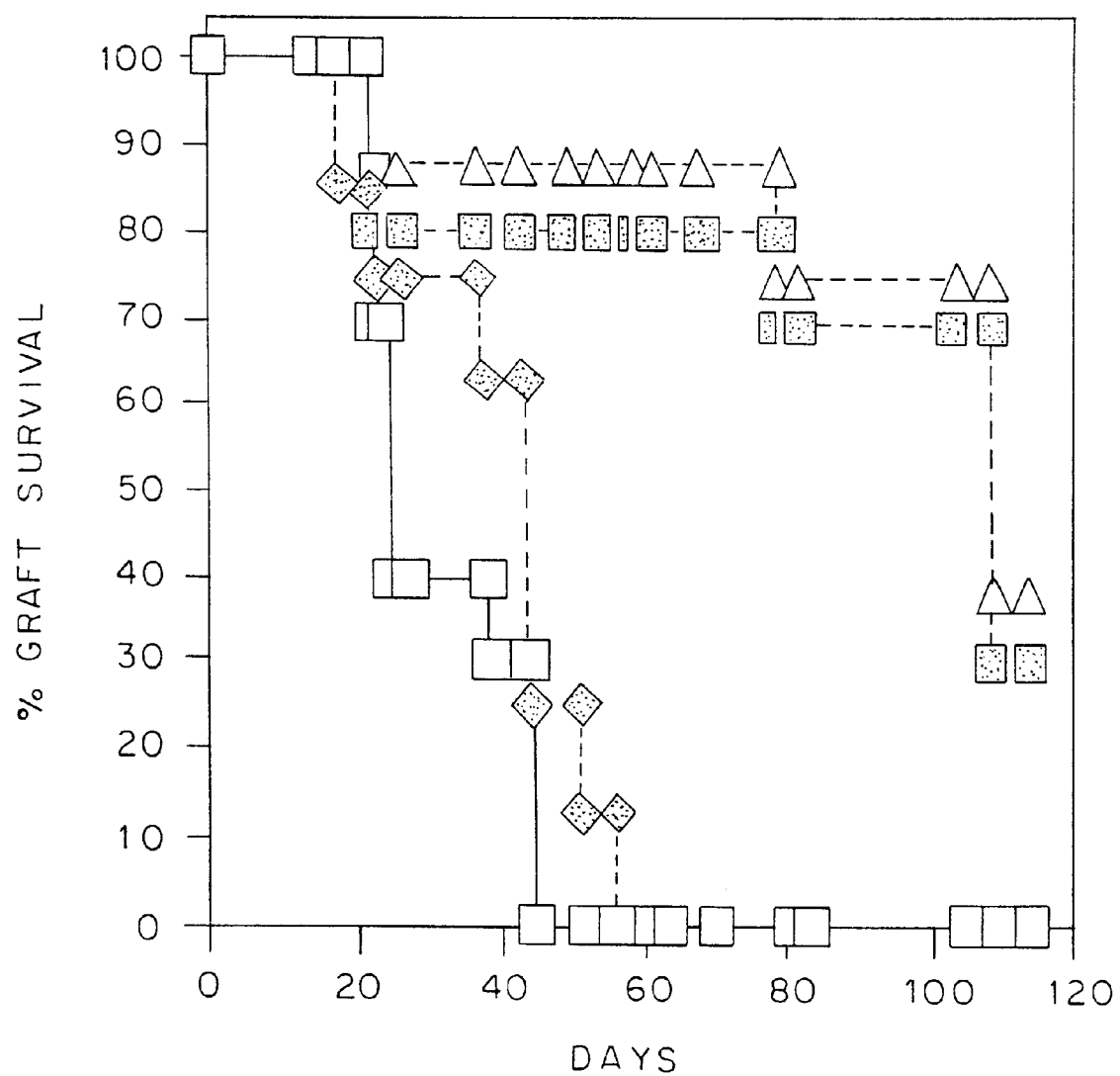

FIG. 4 shows that treatment with hsp60 peptides induces delayed rejection of skin allografts. Wild-type NOD (H-2$^{g7}$) mice were treated with various hsp60 peptides in incomplete Freund's adjuvant. Peptides of the mouse hsp60 sequence were synthesized and purified as described (Elias et al 1991). The sequence of peptide p11 is Val-Ile-Ala-Glu-Leu-Lys-Lys-Gln-Ser-Lys-Pro-Val-Thr-Thr-Pro-Glu-Glu-Ile-Ala-Gln (SEQ ID NO:11) and that of peptide p12 is Glu-Glu-Ile-Ala-Gln-Val-Ala-Thr-Ile-Ser-Ala-Asn-Gly-Asp-Lys-Asp-Ile-Gly-Asn-Ile (SEQ ID NO:9). Peptide p277 is the V-substituted human p277 peptide Val-Leu-Gly-Gly-Gly-Val-Ala-Leu-Leu-Arg-Val-Ile-Pro-Ala-Leu-Asp-Ser-Leu-Thr-Pro-Ala-Asn-Glu-Asp (SEQ ID NO:7) previously described (Elias et al 1991) and shown to be cross-reactive with the mouse p277 homolog (Birk et al 1996a). Control mice were untreated (open square) or were treated with incomplete Freund's adjuvant containing 50 μg of peptide p11, a control non-immunogenic hsp60 peptide (closed diamond). The differences in rejection between treatment with p12 (closed square) or p277 (open triangle) and the controls were significant ($p<0.0001$). Each group contained 10–12 mice.

DETAILED DESCRIPTION OF THE INVENTION

The present invention is based on the discovery that hsp60 autoimmunity functions as an accelerator of foreign immunity and the further discovery that down-regulation of hsp60 autoimmunity suppresses or prevents the graft rejection reaction. Accordingly, the process in accordance with the present invention reduces the vigor of the host vs graft reaction (HVGR) and permits a reduction in the doses of immunosuppressive drugs, such as cyclosporin and prednisone, needed to maintain the graft. The therapy of the present invention is preferably administered concomitantly with the immunosuppressive drug treatment, but the doses of the drugs will be much lower and cause fewer side effects.

Down-regulation of hsp60 autoimmunity is already well known for other indications such as the prevention or treatment of IDDM or incipient IDDM. Such techniques are known to include administration of hsp60, peptides of the hsp60 molecule or variants thereof with a tolerogenic carrier in order to create tolerance for hsp60 and thus down-regulate the hsp60 autoimmune attack or with a biologically active carrier which mediates a TH1→TH2 shift. It is known that hsp60 autoimmunity can be down-regulated whenever a shift is caused from hsp60 T cells which are predominantly of the TH1 type to hsp60 T cells which are predominantly of the TH2 type. Thus, the use of a biologically active carrier in such a vaccine which causes or mediates such a TH1→TH2 shift is preferred for accomplishing such hsp60 autoimmunity down-regulation.

Another method known in the art for down-regulating hsp60 autoimmunity involves the activation of autologous T cells ex vivo against hsp60 or peptides or variants thereof and then re-administering them to the host so as to cause an immune response to be mounted against said T cells so as to quell autoimmune anti-hsp60 T cells and thereby down-regulate hsp60 autoimmunity. See U.S. Pat. No. 5,578,303, the entire contents of which are hereby incorporated by reference.

Thus, many ways of down-regulating hsp60 autoimmunity are already known and the present invention is not directed, per se, to such methods of down-regulating hsp60 autoimmunity. The present invention is drawn to the discovery that such down-regulation, when administered to transplant recipients, will prevent or suppress graft rejection. Accordingly, any technique which causes hsp60 autoimmunity down-regulation, when used on transplant recipients, either immediately prior to, simultaneous with or shortly after transplantation, is intended to be encompassed by the present invention.

One preferred method of causing down-regulation of hsp60 autoimmunity is the administration of hsp60 protein or hsp60 peptides or variants as an immunological agent with a tolerogenic or biologically active carrier. The human hsp60 protein sequence is SEQ ID NO:1, and Table 1 lists peptides and peptide analogs of hsp60 that will down-regulate hsp60 autoimmunity. These peptides and analogs have been shown to be useful in preventing or treating the autoimmune process of insulin-dependent diabetes mellitus (IDDM) (see PCT/US96/11375). It will be appreciated by those of skill in the art that the hsp60 protein and the hsp60 peptides identified in Table 1 are non-limiting examples of immunological agents that can be administered as part of a pharmaceutical composition to down-regulate hsp60 autoimmunity and graft rejection. The selection of the protein or peptide immunological agent that may most optimally be used for an individual transplant recipient is discussed later in this section.

TABLE 1

| Peptides | SEQ ID NO: (residues) |
| --- | --- |
| p3 | 1 (31–50) |
| p10 | 1 (136–155) |
| p11 | 1 (151–170) |
| p12 | 1 (166–185) |
| p14 | 1 (195–214) |
| p18 | 1 (255–274) |
| p20 | 1 (286–305) |
| p24 | 1 (346–365) |
| p29 | 1 (421–440) |
| p30 | 1 (436–455) |
| p32 | 1 (466–485) |
| p35 | 1 (511–530) |
| p39 | 1 (343–366) |
| p278 | 1 (458–474) |
| p277 | 1 (437–460) |
| p277 (Lys$^{19}$) | 2 |
| p277 (Val$^6$) | 3 |
| p277 (Val$^6$–Lys$^{19}$) | 4 |
| p277 (Val$^{11}$) | 5 |
| p277 (Val$^{11}$–Lys$^{19}$) | 6 |
| p277 (Val$^6$–Val$^{11}$) | 7 |
| p277 (Val$^{6,11}$—Lys$^{19}$) | 8 |
| mouse p12 | 9 |
| mouse p38 | 10 |

Whenever unspecified, the human sequence is intended. The mouse p12 and mouse p38 peptides are derived from the mouse hsp60 protein and correspond to residues 168–188 and 556–573, respectively, of mouse hsp60.

The hsp60 protein or hsp60 peptides used as immunological agent in the pharmaceutical composition administered to prevent or suppress graft rejection are intended to encompass salts and functional derivatives thereof, as well as hsp60 peptide analogs, such as those exemplified for peptide p277 in Table 1, as long as the biological activity of the protein or peptide with respect to down-regulating hsp60 autoimmunity is maintained.

Variants of hsp60 peptide p277, herein referred to as "peptide analogs", where the sole threonine residue was replaced by a lysine residue and/or one or both of the cysteine residues were replaced by valine residue(s), were previously found in the laboratory of the present inventors to be equally as active as p277 in down-regulating hsp60 autoimmunity as a treatment for IDDM. These same peptide analogs are expected to down-regulate hsp60 autoimmunity when administered to prevent or suppress graft rejection following organ or tissue transplant.

"Salts" of the hsp60 peptides of the invention contemplated by the invention are physiologically acceptable organic and inorganic salts.

"Functional derivatives" of the hsp60 peptides as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof.

These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for examples that of seryl or threonyl residues) formed by reaction with acyl moieties.

The hsp60 autoimmunity down-regulation treatment is preferably administered immediately prior to the transplant operation. The term "immediately prior" is intended to comprehend a period of time during which the down-regulation of hsp60 autoimmunity accomplished by such treatment still remains in the host, preferably at a time such that the optimal down-regulation coincides with the time of the transplant. The hsp60 autoimmunity down-regulation treatment may also be administered simultaneously with the transplant or shortly thereafter. The term "shortly thereafter" is intended to include a time period such that the hsp60 autoimmune down-regulation occurs prior to the onset of substantial graft rejection.

In the present invention, administration of the pharmaceutical composition containing hsp60, hsp60 peptides, or analogs thereof, as immunologically active agents to down-regulate hsp60 autoimmunity in a recipient can be through various routes known in the art, such as orally, intranasally, intravenously, intramuscularly, or subcutaneously. Preferred modes of administration are intravenously, which is known to induce tolerance, or orally or intranasally, which are known to induce a TH1→TH2 shift. See Wraith et al., 1995; Metzler et al., 1996; Metzler et al., 1995; Tian et al., 1996; Daniel et al., 1996; Weiner et al., 1994. The preferred dosage of the hsp60 protein, or peptides and analogs thereof, is in the range of about 100 µg to 25–30 mg prior to transplantation of organ or tissue. Optimum dosages and regimens can be determined by those of skill in the art by measuring for a shift from TH1 cytokine response to a TH2 cytokine response.

While it is preferred to administer the hsp60 immunological agents prior to transplantation, depending on the level of down-regulation of hsp60 autoimmunity, further administration of hsp60 protein, or peptides or analogs thereof, may be given after transplantation to further reduce or down-regulate the level of hsp60 autoimmunity. Likewise, vaccination with T cells specific to the hsp60 immunological agents and which have been activated in vitro by contact with the hsp60 immunological agents, can will also down-regulate hsp60 autoimmunity and suppress graft rejection after transplantation.

The administration of the hsp60 immunological agents is preferably concomitant with the administration of conventional immunosuppressive therapy, although the reduction in the severity of the HVGR will permit a reduction in the dose of the conventional immunosuppressive drugs, such as cyclosporin and prednisone.

Graft rejection was found to be regulated by hsp60 autoimmunity and the suppression or prevention of hsp60 autoimmunity following organ or tissue transplantation is not associated with T cell tolerance or anergy, but rather is associated with a shift in the cytokines produced by autoimmune T cells reactive to hsp60 or hsp60 peptides from a TH1-like profile (producing IL-2, IFNγ) to a TH2-like profile (IL-4, IL-10). The association of hsp60 protein or hsp60 peptide administration with a switch in reactivity to these immunological agents from T-cell proliferation to antibodies indicates that the protective effect results from a shift in the predominant cytokines produced by the autoimmune T cells in the treated subject. TH1 cells secrete IL-2, which induces T-cell proliferation, and cytokines such as IFN-γ, which mediate tissue inflammation, thereby contributing to the inflammatory response against transplanted organs or tissues; TH2 cells, in contrast, secrete IL-4 and IL-10. IL-4 helps B cells secrete antibodies of certain IgG isotypes and suppresses the production of TH1 inflammatory cytokines. IL-10 indirectly inhibits TH1 activation by affecting antigen-presentation and inflammatory cytokine production by macrophages. Thus, TH2 cells suppress TH1 activity (see Liblau et al., 1995). The shift from TH1 to TH2-like behavior was supported by analysis of the isotypes of the antibodies produced before and after peptide p277 therapy in its use as a treatment for IDDM. Any concomitant treatment that augments this TH1→TH2 shift may also be used in conjunction with the present invention.

It is expected that different epitopes of the hsp60 protein may be more important in the hsp60 autoimmunity in different individuals. It is known, for example, that individuals of different human leukocyte antigen (HLA)-type have different HLA molecules. The different types of HLA molecules each have their individual peptide binding motifs. Thus, in a preferred embodiment of the present invention, the autologous peripheral blood lymphocytes of the intended recipient can be screened against a panel of hsp60 peptides to see which peptide has the optimum effect on the hsp60 autoimmunity. It is well-established in the art that class II MHC molecules bind to peptides 12–15 amino acid residues in length, with a minimum length perhaps as short as 9 amino acid residues, and that class I MHC molecules bind peptides of 7–9 amino acid residues. Thus, peptides of hsp60, such as those presented in Table 1, can be readily screened to determine one or more optimal peptides that can be administered to a particular individual recipient, or to a recipient of a given HLA-type, to shift to a TH2 cytokine response and thereby down-regulate his/her own hsp60 autoimmunity. The optimum peptide should remain the same for different individuals of the same HLA-type.

Eventually, greater knowledge about the peptide binding motifs of HLA molecules will permit a prediction of which peptides will best fit in the cleft and be presented. Until that time, screening techniques such as any of the following can be used.

Peripheral blood lymphocytes (PBL) of an individual human recipient can be isolated from whole blood by Ficoll-Hypaque density gradient centrifugation as is well-known in the art. This sample of the recipient's lymphocytes can be tested for binding to the peptides to be screened in accordance with the method disclosed in Mozes et al., U.S. Pat. No. 5,356,779, or can be tested for in vitro T-cell proliferation and subsequent T-cell cytokine response as assays to determine an optimal or near optimal hsp60 peptide for a specific individual recipient. Mozes et al., U.S. Pat. No. 5,356,779, herein incorporated by reference, discloses direct binding of peptides, that are T cell epitopes, to human antigen-presenting cells (APC) in peripheral blood lymphocytes isolated from whole blood by Ficoll-Hypaque density gradient centrifugation. Detection of the bound T cell epitope is achieved by monitoring, for instance, a fluorescent probe, such as phycoerythrin and its analogs, that is covalently conjugated to the peptide epitope. Thus, a panel of overlapping peptides of seven to fifteen amino acid residues in length from the entire length of the hsp60 protein can be prepared and screened for binding to the recipient's APC's. Those which optimally bind are those which are preferred for use with that particular recipient in down regulating hsp60 autoimmunity.

Another way to screen this panel of peptides is to test the recipient's lymphocytes for in vitro proliferation in the presence of each of the peptides of the panel or to test for TH1→TH2 shift caused by such peptides. Thus, supernatants of T-cells cultured with test peptides at concentrations of 5–50 µg/ml may be collected at different time points and tested for the activity of various cytokines, such as IFNγ and IL-4 secreted into the culture medium, which can be quantitated by ELISA using standard ELISA protocols, or for the presence of antibodies of particular classes.

For example, it is known that in mice TH1 type T cells induce the production of antibodies of the IgG2a class, while TH2 type antibodies induce the production of antibodies of the IgG1 class. While the human equivalents are not yet well defined, once the difference is established, assaying for the isotype of antibodies to the hsp60 immunological agent can be used to monitor the shift from a TH1 T cell response to a TH2 T cell response. It is known, for example, that in humans the IgE isotype is induced by TH2 cells.

Similarly, it is known that TH1 cells secrete cytokines which induce T cell proliferation, and cytokines such as IFNγ, which mediate tissue inflammation. On the other hand, TH2 cells secrete IL-4, which helps β-cells secrete antibodies of the IgG and IgE class and suppress the production of TH1 inflammatory cytokines, as well as IL-10, which indirectly inhibits TH1 activation by affecting antigen presentation and inflammatory cytokine production by macrophages. Accordingly, a measurement of the cytokine profile of the in vitro proliferated T cells will also be an indication of a shift from a TH1 T cell response to a TH2 T cell response. Thus, the TH1→TH2 shift can serve as a marker for monitoring the in vitro response of a recipient's T lymphocytes to various test peptides in determining optimal or near optimal peptides.

Specific techniques for assaying the isotype of antibodies and for assaying the presence of various cytokines are not per se a novel part of the present invention. Those of ordinary skill in the art are well aware of various manners of assaying for antibody isotype or for the various cytokines produced by TH1 and TH2 T cells. Any such techniques can be used in the course of the present invention for detecting a TH1 to TH2 shift. The examples presented herein disclose illustrative manners of doing so, but it is not intended that the present invention be limited thereto.

When the technique elected for hsp60 autoimmunity down-regulation is the administration of hsp60 or a peptide or a variant thereof the carrier or adjuvant selected must be one which creates tolerance to the peptide being administered or which actively induces a TH1→TH2 shift. Otherwise, the autoimmune response could actually be up-regulated. Examples of such known tolerogenic carriers include mineral oil carriers such as incomplete Freund's adjuvant (IFA). IFA is an emulsion of mineral oil. However, IFA is not allowed for human use because mineral oil is not metabolizable and cannot be degraded by the body.

Biologically active carriers which augment the TH1→TH2 shift are particularly preferred in accordance with the present invention. It has recently been found that certain fat emulsions, which have been in use for many years for intravenous nutrition of human patients, can also act as a biologically active vehicle for peptide therapy using the peptides of the present invention. Two examples of such emulsions are the commercially available fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin. These fat emulsions are quite stable and have been used for intravenous nutrition of patients suffering from gastrointestinal or neurological disorders, which prevent them from receiving nutrition orally, and thus, they receive the calories needed to sustain life. Usual daily doses for intravenous nutrition are up to 1 liter daily.

While Intralipid and Lipofundin are preferred examples of biologically active carriers for the protein or peptide immunological agent administered as a treatment for suppressing or preventing graft rejection, any pharmaceutically acceptable carrier, in particular lipid carriers, which causes a shift from TH1 response to TH2 response can be used in the pharmaceutical compositions of the present invention. Preferably, such biologically active lipid carriers comprise a fat emulsion containing 10–20% triglycerides of plant and/or animal origin, 1.2–2.4% phospholipids of plant and/or animal origin, 2.25–4.5% osmo-regulator, 0–0.05% anti-oxidant, and sterile water to 100%. Intralipid and Lipofundin are the most preferred examples of this preferred fat emulsion. The triglycerides and phospholipids of plant or animal origin may be derived from any suitable vegetable oil, such as soybean oil, cottonseed oil, coconut oil or olive oil, or from egg-yolk or bovine serum. Preferably, the triglycerides/phospholipids weight ratio is about 8:1.

Any suitable osmo-regulator may be added to the fat emulsion, preferably glycerol, xylitol or sorbitol. The fat emulsion may optionally include an anti-oxidant, for example 0.05% tocopherol.

A preferred biologically active carrier which may be used with the present invention is a fat emulsion containing 10% soybean oil, 1.2% egg-yolk phospholipids, 2.5% glycerol and sterile water to complete 100 ml (Intralipid 10). In another embodiment, the vehicle is a fat emulsion containing 20% soybean oil, 2.4% egg-yolk phospholipids, 2.5% glycerol and sterile water to complete 100 ml.

In another preferred embodiment, the vehicle is a fat emulsion containing 5% soybean oil and another 5% triglycerides from animal origin, e.g., 5% medium chain triglycerides from butter, 1.2% egg-yolk lecithin, 2.5% glycerol and distilled water to complete 100 ml (Lipofundin 10%). In yet another preferred embodiment of the biologically active lipid carrier, the fat emulsion as defined above is processed by centrifugation, e.g., at 10,000 g or higher, thus forming a small triglyceride-rich (about 90% triglycerides) layer on the top of a phospholipid-enriched aqueous dispersion containing about 1:1 triglycerides:phospholipids, and this latter aqueous dispersion is used as the lipid vehicle in the pharmaceutical compositions of the invention.

The fat emulsions which may be used in the present invention are preferably used when freshly prepared or after storage within a container which is not open to the atmosphere. Prolonged storage of Intralipid, for example, in the presence of atmospheric air, causes a decrease in pH and a corresponding decrease in biological activity.

The effectiveness of the hsp60 autoimmunity downregulation may be monitored in the host by monitoring the TH1→TH2 shift therein. This may be accomplished in the manner described in PCT/US96/11374, the entire contents of which are hereby incorporated herein by reference.

Having now generally described the invention, the same will be more readily understood through reference to the following example which is provided by way of illustration, and is not intended to be limiting of the present invention. The example described herein establish as the effectiveness of the present invention in a scientifically accepted mouse model for skin allograft survival.

EXAMPLE 1

To establish whether natural autoimmunity to hsp60 is merely compatible with health, or whether natural hsp60 autoimmunity actually contributes to the function of the immune system, the laboratory of the present inventors developed an hsp60 transgenic NOD mouse which hyperexpresses mouse hsp60 under the direction of the promoter of the major histocompatibility complex (MHC) class II Eα molecule (Birk et al., 1996b). These mice express high amounts of hsp60 in the thymus and in antigen-presenting cells (APC) throughout the body, resulting in a relative loss of their otherwise spontaneous hsp60 autoimmunity. Study of the spontaneous autoimmune diabetes in these transgenic NOD mice has demonstrated that hsp60 autoimmunity is critical to the destruction of the self-beta cells (Birk et al., 1996b). As presented below, the Eα-hsp60 transgenic mice are exploited either as donors of skin enriched in self-hsp60 expression, or as recipients of foreign skin.

The present inventors have discovered that hsp60 is over-expressed in rejected skin allografts, and that in the Eα-hsp60 transgenic mice such overexpression was demonstrated to have a functional TH1-mediated role in allograft rejection. In addition, allograft rejection can be delayed and even prevented by therapeutic modulation of hsp60 autoimmunity. The results of these experiments are described below.

Figure 1:
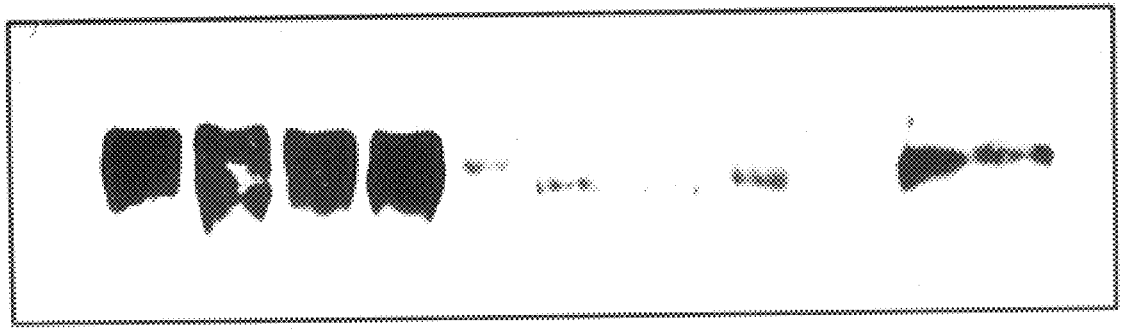
FIG. 1 shows the expression of hsp60 in mouse skin. Lanes 1–4 each show hsp60 expression during rejection of BALB/c (H-$2^d$) skin removed 10 days after transplantation to allogeneic NOD (H-$2^{g7}$) mice. Lanes 5–8 show the expression of hsp60 in BALB/c skin transplanted 10 days earlier to syngeneic BALB/c mice. Lane 9 shows the spontaneous expression of hsp60 in untransplanted Eα-hsp60 transgenic NOD skin. Lane 10 shows the expression of hsp60 in untransplanted wild type NOD skin.

FIG. 1 shows the expression of mouse hsp60 in wild type mouse skin transplanted to allogenic hosts and undergoing rejection (lanes 1–4), or transplanted to syngeneic hosts and tolerated (lanes 5–8). Shaved skin was removed surgically and lysed in TENN buffer (50 mM Tris, pH 8.0, 5 mM EDTA, 0.5% NP-40, 150 mM NaCl). Equal amounts of protein (50 μg, determined using the Bradford reagent, Biorad) were fractionated on 10% SDS-PAGE and transferred to nitrocellulose paper (Towbin et al., 1979) for Western blot analysis using LK1, a monoclonal antibody specific for hsp60 (Boog et al., 1992) at a 1:500 dilution, and the ECL detection system (Amersham, UK). It can be seen by comparing lanes 1–4 to 5–8 that the process of rejection augments the expression of hsp60 in wild type skin. Thus, the heightened expression of hsp60 in the target of rejection process appear to allow hsp60 autoimmunity to play a role in the graft rejection process.

To explore this question, the laboratory of the present inventors used the transgenic mice. FIG. 1 also shows that the expression of hsp60 is constitutively augmented in Eα-hsp60 transgenic NOD skin (lane 9) compared to that in wild type NOD skin (lane 10), probably due to activation of the MHC class II promoter in skin dendritic cells (Kampgen et al, 1991). The consequences of this constitutive hyperexpression are shown in FIG. 2, where one $cm^2$ sections of skin were cut from the backs of sacrificed donor mice and washed in saline. Patches of dorsal skin of one $cm^2$ were removed from anesthetized recipient mice treated with Nembutal 6 mg/ml, 0.25 ml per mouse and replaced by the donor skin grafts. Histoacryl (B. Braun Meleungen AG, D-34209 Melsungen, Germany) was applied around the grafts and Nobecutan (ASTR, Astra Tech, POB 13, Glos G15, UK) was sprayed over them.

Figure 2A:
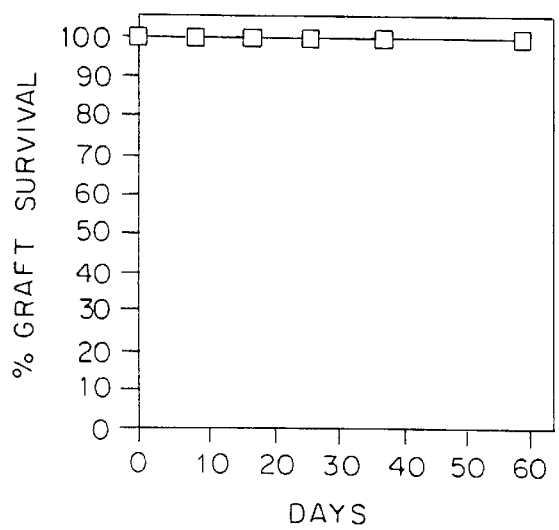
FIGS. 2A–F show that the expression of hsp60 affects allogeneic skin rejection as measured by graft survival over time. Statistical analysis of skin graft survival was done using the Wilcoxon test.
Figure 2B:
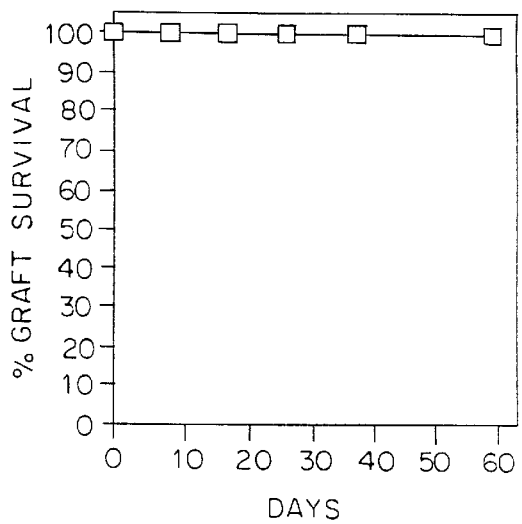
Figure 2C:
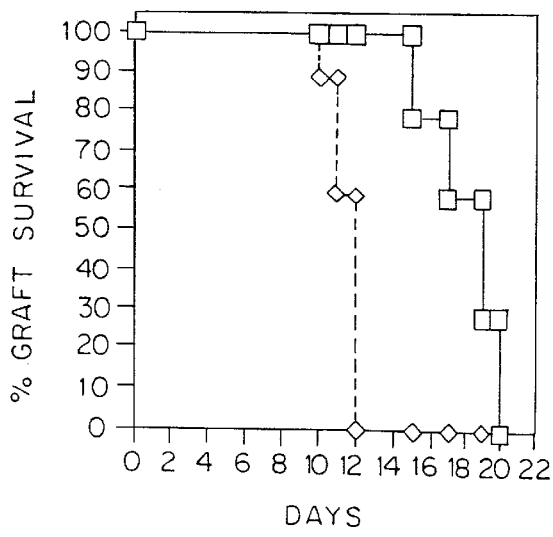
Figure 2D:
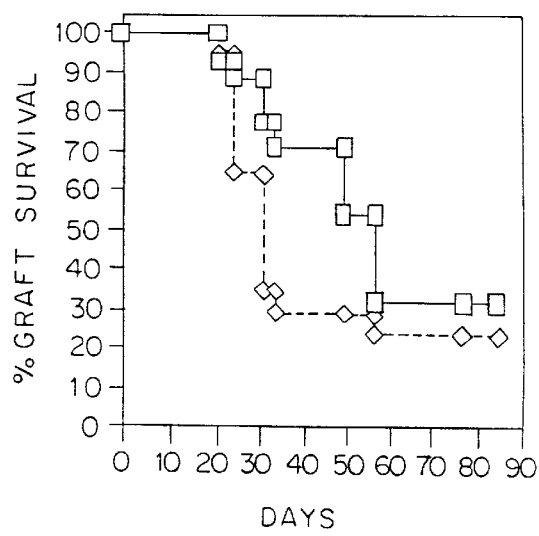

FIGS. 2A and 2B show that the Eα-hsp60 NOD transgenic skin is not rejected when transplanted to non-transgenic NOD recipient mice. Thus, the hsp60 transgenic skin has not acquired a foreign histocompatibility antigen during insertion of the mouse hsp60 transgene; Eα-hsp60 transgenic skin is still self. Nevertheless, FIGS. 2C and 2D show that the hyperexpressed Eα-hsp60 transgene can markedly augment the allograft rejection in two different rejection systems. FIG. 2C shows acceleration of skin rejection across the MHC barrier (NOD $H2^{g7}$ skin transplanted to allogeneic BALB/c $H-2^d$ mice), the median day of rejection being reduced from 20 to 12 days (p<0.0001), while FIG. 2D shows acceleration of the rejection by female NOD recipients of male Eα-hsp60 transgenic NOD skin compared to rejection of wild-type male skin, the median day of rejection being reduced from 55 to 30 days (p<0.038). The rejection of male skin by syngeneic female mice is caused by a minor histocompatibility antigen encoded by the male Y chromosome (Scott et al., 1995). Thus, the constitutive hyperexpression of self-hsp60 in donor transgenic skin augments the rejection process directed to foreign transplantation antigens, either major or minor.

Figure 2E:
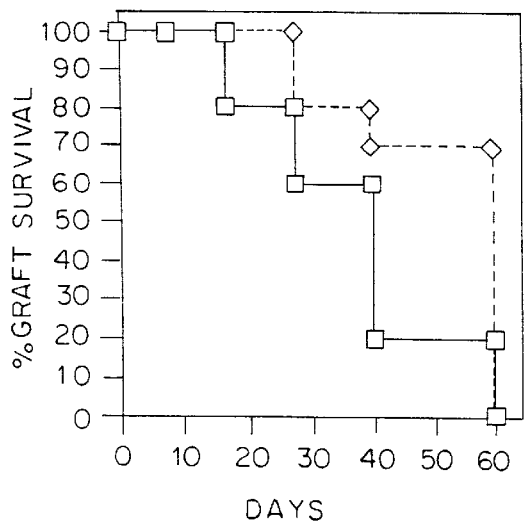
Figure 2F:
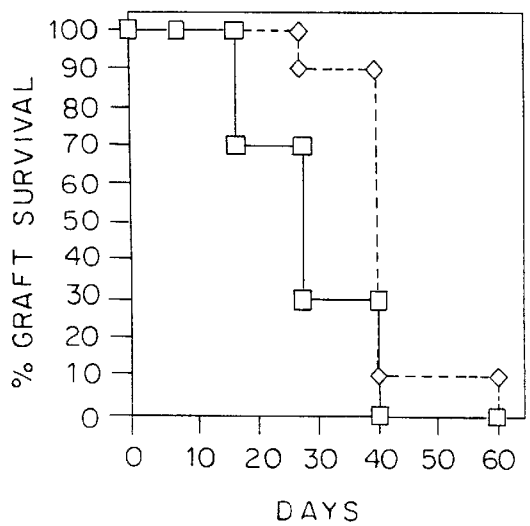

FIGS. 2E and 2F show the converse experiment where the recipient NOD mice are bearers of the Eα-hsp60 transgene and thus have depressed hsp60 autoimmunity (Birk et al, 1996b). Compared to wild type NOD mice, the Eα-hsp60 transgenic mice manifested a delayed median day of rejection of allogeneic C57BL/6 ($H-2^b$) skin grafts (FIG. 2E) by 20 days (p=0.004) and of BALB/k (H-2k) skin grafts (FIG. 2F) by 10 days (p=0.0001). Rejections of BALB/c ($H-2^d$) and BALB/b ($H-2^b$) skins were also significantly delayed (p=0.001 an p=0.015, respectively), not shown. Thus, mice with depressed anti-hsp60 autoimmunity manifest a depressed allograft rejection reaction.

The laboratory of the present inventors have previously found that hsp60 autoimmunity can be modulated in wild type NOD mice (Elias et al., 1990; Elias et al., 1991; Elias et al., 1994; Elias et al., 1995) and in other strains (Elias et al., 1996) by therapeutically vaccinating the mice subcutaneously with whole hsp60 or hsp60 peptides emulsified in mineral oil (incomplete Freund's adjuvant; IFA). The mechanism of modulation (Elias et al, 1996) appears to involve a shift in the phenotype of the T-cell response to hsp60 from a proinflammatory TH1 type to an anti-inflammatory TH2 type of response (Finkelman et al, 1990).

FIGS. 3A-14 3B show that such vaccination of wild type NOD ($H-2^{g7}$) recipient mice or of C57BL/6 ($H-2^b$) mice two weeks before transplantation of BALB/c ($H-2^d$) skin caused a delay in skin allograft rejection. It can be seen in FIG. 3A that C57BL/6 mice, a strain not known to suffer from spontaneous autoimmune diseases, manifested significantly prolonged survival of BALB/c skin grafts after vaccination with hsp60 ($p<0.01$). C57BL/6 mice that had been vaccinated with IFA alone or with the control recombinant antigen glutathione transferase did not manifest prolonged survival of the BALB/c skin. It can be seen in FIG. 3B that NOD mice also manifested delayed rejection of BALB/c allogeneic skin following hsp60 vaccination compared to vaccination with the control recombinant antigen ($p<0.0001$). FIG. 4 shows that vaccinating NOD mice with hsp60 peptides also prolonged the survival of the allogeneic BALB/c skin ($p<0.001$). It can be seen that hsp60 peptides p12 and p277 were effective compared to untreated mice. In contrast, peptide p11, which is not immunogenic in NOD mice, did not prolong survival of the skin allograft. Treatment of NOD mice with an immunogenic peptide of Mycobacterial hsp60, which is not cross-reactive with self-hsp60, also did not prolong survival of the allograft (not shown). Thus, vaccination with hsp60 or various hsp60 peptides, shown previously to modulate spontaneous hsp60 autoimmunity (Elias et al., 1990; Elias et al., 1991; Elias et al., 1994; Elias et al., 1995; Elias et al., 1996), can significantly inhibit the rejection of foreign skin.

As is shown in FIG. 1, the stress of the transplantation reaction can up-regulate hsp60 expression even in wild type, non-transgenic skin. T cells reactive to hsp60 and other hsp molecules have been isolated from cardiac allografts (Moliterno et al., 1995) as well as from other inflammatory lesions (Selmaj et al., 1991; Mor et al., 1992). Thus, anti-hsp60 autoimmune T cells accumulate at sites of inflammation. It is theorized that the constitutive hyper-expression of hsp60 in the donor Eα-hsp60 skin amplifies the activation of anti-hsp60 autoimmune T cells at the site and enhance the local immune response by adding pro-inflammatory (TH1-type) cytokines, such as INFγ (Finkelman et al., 1990), to the allograft reaction, thereby inciting and abetting other T cells responsive to the foreign antigens. Conversely, hsp60 autoimmune T cells that have been activated to produce anti-inflammatory cytokines of the TH2-type, such as IL-10, should serve to shut down the effector immune reaction by a form of by-stander suppression (Weiner et al., 1994). To test whether treatment with hsp60 peptides might modify the cytokine response, NOD or C57BL mice were treated with hsp60 or with hsp60 peptide p12. Control mice were untreated or were treated with saline emulsified in IFA. The mice were grafted with BALB/c skin grafts and twenty days later, just at the beginning of graft rejection in the control mice, groups of 5–10 mice were sacrificed and their spleen cells assayed individually in a standard mixed lymphocyte reaction (MLR) with irradiated BALB/c spleen cells as stimulators (Lohse et al., 1990). The MLR cultures were tested for T-cell proliferation by thymidine incorporation (Lohse et al., 1990) and no significant differences were found between the treated and control groups. However, the MLR media were also tested for the presence of the TH1 cytokine IFNγ and the TH2 cytokine IL-10. It was found that the control mouse T cells produced 9.25±1.7 ng/ml of IFNγ, while the T cells from the hsp60 and p12 treated mice produced only 3.13±1.4 ng/ml of IFNγ ($p=0.002$). In contrast to the decrease in IFNγ, the treated mice showed increased production of IL-10; 8±1.4 ng/ml compared to 3.5±0.6 ng/ml in the control mice ($p=0.004$). Thus, prolongation of the survival of skin allografts induced by vaccination with hsp60 or hsp60 peptides was associated with decreased IFNγ and increased IL-10 secreted during the MLR in vitro. It was also found that the Eα-hsp60 transgenic NOD mice manifest a specific decrease in their IFNγ (TH1) response to hsp60. These findings suggest that modulation of the allograft reaction by hsp60 autoimmunity may be mediated by differential cytokine production. But irrespective of the mechanism, the present results demonstrate that hsp60 autoimmunity can be critical in the response to foreign antigens, strong or weak. Hence, natural autoimmunity to hsp60, and possibly to the other natural self antigens registered in the immunological homunculus (Cohen 1992a; Cohen 1992b), have a regulatory role.

Beyond theoretical speculation, manipulating hsp60 autoimmunity can have practical benefits. The laboratory of the present inventors has shown elsewhere that natural hsp60 autoimmunity can be exploited to induce T-cell help for a response to poorly immunogenic bacterial antigens through the use of hsp60 peptide-bacterial sugar conjugates (Konen-Waisman et al, 1995). Hence, up-regulating autoimmunity to hsp60 can help fight infection. The present invention establishes that down-regulating natural hsp60 autoimmunity is useful in thwarting graft rejection.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abas, A. K. et al., eds., "Cellular and Molecular Immunology", 2nd ed. W. B. Saunders Co., pp. 239–260 (1994).

Birk et al. *Opin. Immunol.* 5:903–909 (1993).

Birk et al. *J. Autoimm.* 9:159–166 (1996a).

Birk et al. *Proc. Natl. Acad. Sci. (USA)* 93:1032–1037 (1996b).

Boog, C. J. et al. *J. Exp. Med.* 175:1805–1810 (1992).

Cohen, I. R. *Annu. Rev. Immunol.* 9:576–589 (1991).

Cohen, I. R. *Immunol. Today* 13:441–444 (1992a).

Cohen, I. R. *Immunol. Today* 13:490–494 (1992b).

Daniel, D. et al. *Proc. Natl Acad Sci (USA)* 93:956–960 (1996).

Elias, D. et al. *Proc. Natl Acad Sci (USA)* 87:1576–80 (1990).

Elias, D. et al. *Proc. Natl Acad Sci (USA)* 88:3088–3091 (1991).

Elias, D. et al. *Lancet* 343:704–706 (1994).

Elias, D. et al. *Diabetes* 44:1132–1138 (1995).

Elias, D. et al. *Diabetes* 45:1168–1172 (1996).

Finkelman, F. D. et al. *Annu. Rev. Immunol.* 8:303–333 (1990).

Hogervorst, E. J. M. et al. *Intern. Immunol.* 4:719 (1992).

Kampgen, E. et al. *Proc. Natl. Acad. Sci. (USA)* 88:3014–3018 (1991).

Kaufmann, S. H. E. *Immunol. Today* 11:129–36 (1990).

Kaufmann, S. H. E. *The Biology of Heat Shock Proteins and Molecular Chaperones* (1994).

Konen-Waisman, S. et al. *J. Immunol.* 5977–5985 (1995).

Kristiansen, T. et al. *J. Biosci.* 5 (suppl. 1):149–155 (1983).

Lohse, A. W. et al. *Eur. J. Immunol.* 20:2521–2524 (1990)

Liblau, R. S. et al. *Immunology Today* 16:34–38 (1995).

Metzler, B. et al. *Adv. Exp. Med. Biol.* 371B:1243–1244 (1995).

Metzler, B. et al. *Ann. N.Y. Acad. Sci.* 778:228–242 (1996).

Moliterno, R. et al. *Transplantation* 59:594 (1995).

Moore, K. V. et al. *Ann. Rev. Immunol.* 11:165–190 (1993).

Mor, F. et al. *J. Clin. Invest.* 90:2447–2455 (1992).

Mosmann, T. R. et al. *Ann. Rev. Immunol.* 7:145–173 (1989).

Res et al. *Lancet* 2:478–480 (1989).

Romagnani, S., *Ann. Rev. Immunol.* 12:227–257 (1994).

Scott, D. M. et al. *Nature* 376:695–698 (1995).

Selmaj, K. et al. *Proc. Natl. Acad. Sci. (USA)* 88:6452–6456 (1991).

Tian, J. et al. *J. Exp. Med.* 183:1561–1567 (1996).

Towbin, H. et al. *Proc. Natl. Acad. Sci. (USA)* 7:4350–4354 (1979).

van Eden, W. et al. *Br. J. Rheumatol.* 28 Suppl:1–3 (1989).

Weiner, H. L. et al. *Annu. Rev. Immunol.* 12:809–37 (1994).

Wraith, D. C. et al. *Ther. Immunol.* 2:53–58 (1995).

Young, R. A. et al. *Cell* 59:5–8 (1989).

---

What is claimed is:

1. A method for reducing the severity of host vs graft reaction, comprising:

immediately prior to, simultaneously with, or shortly after transplantation of donor organ or tissue to a host, specifically down-regulating hsp60 autoimmunity in the host by administering a pharmaceutical composition comprising a tolerogenic carrier, or a biologically active carrier capable of mediating a TH1→TH2 shift, and a compound selected from the group consisting of hsp60, biologically active hsp60 peptides capable of down-regulating hsp60 autoimmunity, and biologically active analogs, salts and functional derivatives thereof which are capable of down-regulating hsp60 autoimmunity.

2. A method in accordance with claim 1, wherein said compound is selected from the group of hsp60 peptides consisting of those having the sequence corresponding to the following amino acid residues from SEQ ID NO:1 : residues 31–50, residues 136–155, residues 151–170, residues 166–185, residues 195–214, residues 255–274, residues 286–305, residues 346–365; residues 421–440, residues 436–455, residues 437–460, residues 466–485, residues 511–530, residues 343–366, and residues 458–474, and biologically active salts and functional derivatives thereof.

3. A method in accordance with claim 2, wherein said compound has the sequence corresponding to residues 437 to 460 of SEQ ID NO:1.

4. A method in accordance with claim 2, wherein said compound has the sequence corresponding to residues 166 to 185 of SEQ ID NO:1.

5. A method in accordance with claim 2, wherein said compound has the sequence corresponding to residues 466 to 485 of SEQ ID NO:1.

6. A method in accordance with claim 1, wherein said compound is an hsp60 peptide analog selected from the group consisting of peptides having the sequence of SEQ ID NO:2, SEQ ID NO:3, SEQ ID NO:4, SEQ ID NO:5, SEQ ID NO:6, SEQ ID NO:7 and SEQ ID NO:8.

7. A method in accordance with claim 1, wherein said biologically active carrier is a fat emulsion comprising:

10–20% triglycerides of plant and/or animal origin;
    1.2–2.4% phospholipids of plant and/or animal origin;
    2.25–4.5% osmo-regulator;
    0–0.05% antioxidant; and
    sterile water.

8. A method in accordance with claim 1, wherein said administering step comprises administering said pharmaceutical composition by oral, intranasal, intravenous, intramuscular or subcutaneous administration to the host before transplantation of donor organ or tissue.

9. A method of selecting and using a peptide in reducing the severity of host versus graft reaction, comprising the steps of:

contacting a panel of individual peptides to antigen-presenting cells of peripheral blood lymphocytes isolated from the blood of an individual who is a candidate for organ or tissue transplant, wherein the peptides are detectably labeled and consist of sequences found within the sequence of the protein of SEQ ID NO:1 or analogs of said sequences;

detecting which peptides bind to the antigen-presenting cells;

selecting one or more peptides capable of binding to the antigen-presenting cells; and immediately prior to, simultaneously with, or shortly after transplantation of donor organ or tissue to said individual, specifically down-regulating hsp60 autoimmunity in said individual, or in an individual of the same HLA-type, by administering a pharmaceutical composition comprising a tolerogenic carrier, or a biologically active carrier capable of mediating a TH1→TH2 shift, and one or more of said peptides which have been selected in said selective step.

10. A method for reducing the severity of host vs graft reaction, comprising:

immediately prior to, simultaneously with, or shortly after transplantation of donor organ or tissue to a host, specifically down-regulating hsp60 autoimmunity in the host by administering to the host T cells activated in vitro with hsp60 protein, hsp60 peptides which cause activation of T cells against hsp60, or analogs, salts or functional derivatives thereof which cause activation of T cells against hsp60.

11. A method in accordance with claim 9, wherein said panel of individual peptides are peptides of 7–15 amino acid residues in length from the hsp60 protein of SEQ ID NO:1.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
           (A) LENGTH: 573 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO: 1:

```
Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60
```

-continued

```
Glu Gln Gly Trp Gly Ser Pro Lys Val Thr Lys Asp Gly Val Thr Val
 65                  70                  75                  80

Ala Lys Ser Ile Asp Leu Lys Asp Lys Tyr Lys Asn Ile Gly Ala Lys
                 85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495
```

```
Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570

(2) INFORMATION FOR SEQ ID NO: 2:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Val Leu Gly Gly Gly Cys Ala Leu Leu Arg Cys Ile Pro Ala Leu Asp
1               5                   10                  15

Ser Leu Lys Pro Ala Asn Glu Asp
            20

(2) INFORMATION FOR SEQ ID NO: 3:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Val Leu Gly Gly Gly Val Ala Leu Leu Arg Cys Ile Pro Ala Leu Asp
1               5                   10                  15

Ser Leu Thr Pro Ala Asn Glu Asp
            20

(2) INFORMATION FOR SEQ ID NO: 4:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Val Leu Gly Gly Gly Val Ala Leu Leu Arg Cys Ile Pro Ala Leu Asp
1               5                   10                  15

Ser Leu Lys Pro Ala Asn Glu Asp
            20

(2) INFORMATION FOR SEQ ID NO: 5:

(i) SEQUENCE CHARACTERISTICS:
        (A) LENGTH: 24 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO: 5:

Val Leu Gly Gly Gly Cys Ala Leu Leu Arg Val Ile Pro Ala Leu Asp
1               5                   10                  15

Ser Leu Thr Pro Ala Asn Glu Asp
            20

(2) INFORMATION FOR SEQ ID NO: 6:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Val Leu Gly Gly Gly Cys Ala Leu Leu Arg Val Ile Pro Ala Leu Asp
1               5                   10                  15

Ser Leu Lys Pro Ala Asn Glu Asp
            20

(2) INFORMATION FOR SEQ ID NO: 7:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Val Leu Gly Gly Gly Val Ala Leu Leu Arg Val Ile Pro Ala Leu Asp
1               5                   10                  15

Ser Leu Thr Pro Ala Asn Glu Asp
            20

(2) INFORMATION FOR SEQ ID NO: 8:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Val Leu Gly Gly Gly Val Ala Leu Leu Arg Val Ile Pro Ala Leu Asp
1               5                   10                  15

Ser Leu Lys Pro Ala Asn Glu Asp
            20

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:9:

```
Glu Glu Ile Ala Gln Val Ala Thr Ile Ser Ala Asn Gly Asp Lys Asp
1               5                   10                  15

Ile Gly Asn Ile
            20
```

(2) INFORMATION FOR SEQ ID NO:10:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Pro Gly Met Gly Ala Met Gly Gly Met Gly Gly Gly Met Gly Gly Gly
1               5                   10                  15

Met Phe
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Glu Glu Ile Ala Gln Val Ala Thr Ile Ser Ala Asn Gly Asp Lys Asp
1               5                   10                  15

Ile Gly Asn Ile
            20
```